United States Patent [19]

Young

[11] Patent Number: 5,317,928
[45] Date of Patent: Jun. 7, 1994

[54] METHOD FOR MEASURING THE FLOW RATE OF A COMPONENT OF A TWO-COMPONENT FLUID MIXTURE

[75] Inventor: Alan M. Young, Los Gatos, Calif.

[73] Assignee: Exac Corporation, San Jose, Calif.

[21] Appl. No.: 6,800

[22] Filed: Jan. 21, 1993

[51] Int. Cl.[5] .......................... G01F 1/74; G01N 9/00
[52] U.S. Cl. .................................. 73/32 R; 73/861.04; 364/577
[58] Field of Search ................. 73/32 R, 61.43, 61.44, 73/861.04, 861.38; 364/510, 558, 577

[56] References Cited

U.S. PATENT DOCUMENTS 4,010,645  3/1977  Herzl ............................ 73/32 R X
4,689,989  9/1987  Aslesen et al. ................ 73/861.04 X

*Primary Examiner*—Herbert Goldstein
*Attorney, Agent, or Firm*—Claude A. S. Hamrick

[57] ABSTRACT

A method for determining the relationship between the density of a multi-component fluid mixture comprising a number of known components and the concentration of one of the components of the fluid mixture. The method comprises the steps of:

(i) determining a first and a second density-concentration relationship to define the relationship between the density of the fluid mixture and the concentration of the component at first and second known temperatures $T_1$ and $T_2$, respectively;

(ii) measuring the temperature T of the mixture;

(iii) determining a temperature ratio value according to the relationship $$\frac{T - T_2}{T_1 - T_2}$$

(iv) choosing a component concentration value $C_i$;

(v) determining first and second density values $\rho(C_i, T_1)$ and $\rho(C_i, T_2)$ by inputing the component concentration value $C_i$ into said first and second density-concentration relationships to yield the first and second density values respectively;

(vi) subtracting the second density value from the first density value to produce a density difference value $\Delta\rho_{T1,T2}$;

(vii) processing the results from steps (iii), (v) and (vi) according to the equation $$\rho(C_i, T) = \rho(C_i, T_2) + \left[ \frac{T - T_2}{T_1 - T_2} \right] * \Delta\rho_{T1,T2}$$

to produce a density-concentration value $\rho(C_i, T)$ for said fluid mixture;

(viii) incrementing the component concentration to provide a new component concentration value $C_i$;

(ix) repeating steps (v) and (viii) until sufficient density-concentration values have been produced to define the relationship between the density of a multi-component fluid mixture comprising a number of known components and the concentration of one of the components of said fluid mixture.

6 Claims, 5 Drawing Sheets

METHOD FOR MEASURING THE FLOW RATE OF A COMPONENT OF A TWO-COMPONENT FLUID MIXTURE

BACKGROUND OF THE INVENTION

1. Field of the Invention

The present invention relates generally to a method for measuring the flow rate of fluids and, more particularly, to a method for measuring the flow rate of a component of a two-component fluid mixture.

2. Brief Description of the Prior Art

In industrial processes involving fluids which are considered to be two-component fluid mixtures, a need exists to accurately measure the concentration of one of the components of the two-component fluid mixture. Typically a two-component fluid mixture consists of either a solid component fully or partially dissolved within a liquid carrier fluid, or a liquid component mixed with a liquid carrier fluid. In addition to measuring the concentration of one of the components of the two-component mixture, a need exists to accurately measure the flow rate corresponding to the measured component.

In the beverage industry, for example, there is a need to accurately measure and control the concentration of sugar in water and to determine the associated total amount of sugar used. In the pulp and paper industry, knowledge of the concentration of $TiO_2$ and its associated flow rate is valuable in accurately controlling paper coating processes. Similarly, in oil production, there is a need to accurately measure the oil and water concentrations and determine the associated oil production rates for royalty calculation purposes.

There are several known prior art methods of measuring the flow rate and/or the concentration of a component of a two-component fluid mixture. One of these methods is described in U.S. Pat. No. 4,689,989 to Aslesen et al. This method is also described in "EXAC Mass Flow Meter Applications Manual (8300 EX, 8310 EX)", pages 2-14 to 2-16.

The method described in these publications is based on the fact that, at a known temperature, a determinable relationship between the density of a two-component mixture and the concentration of one of the components of that mixture exists.

The relationship between the density of the two-component mixture and the concentration of one of the components of that mixture can be plotted graphically as is illustrated by curve 10 in FIG. 1 of the accompanying drawings. In this figure, the density $\rho$ of the two-component mixture is plotted on the vertical axis 12 and the concentration C of one of the components of that mixture is plotted on the horizontal axis 14.

One method of determining the density concentration curve 10 is to create a mixture in which the concentration of one of the components is known. The sample is then heated to a known temperature and its density is measured. If the known component concentration, say $C_1$ and the measured density, say $\rho_1$, are plotted on the vertical and horizontal axes 12 and 14, respectively, a point ($C_1$; $\rho_1$) is defined in the C-$\rho$ plane between the axes 12 and 14.

The above step is then repeated by producing a different sample of the mixture with a different component concentration, say $C_2$, and its measuring density, say $\rho_2$, at the same temperature at which the first concentration $C_1$ and density $\rho_1$ values were measured. This second measurement will yield a further point ($C_2$; $\rho_2$) in the C-$\rho$ plane.

The above process is repeated until sufficient points (typically 15) have been determined to plot the curve 10.

Once this curve has been determined, it can be used to measure the concentration of a component of a two-component fluid mixture. The way this is done is by first measuring the density of a two-component fluid mixture. Typically, this density of the fluid mixture can be measured by using devices such as a pycnometer, a vibrating tube densitometer, gamma ray density gauges, hygrometers, or any other suitable apparatus or technique. This measured density is then plotted on the vertical axis 12, read across to curve 10 and, from curve 10, down to determine the concentration value from the horizontal concentration axis 14.

A major problem with this method is that the curve 10 is derived at a single known temperature and can only be used to determine concentrations in a mixture at that temperature. If this curve 10 is used to determine the concentration of the component of a two-component fluid mixture which is at a different temperature to which the curve 10 was produced, erroneous results will occur.

This can be illustrated by considering the following hypothetical situation: If the density of a two-component fluid mixture is $\rho_1$, the concentration of the measured component of the two-component fluid will, according to curve 10, be equal to $C_1$. This is true, as is described above, only if the temperature of the fluid under consideration is the same as that for which a curve 10 is derived. If that same fluid is now heated to a greater temperature, its density would decrease to a value, say $\rho_3$. If we use curve 10 to determine the concentration of the component of the mixture, this will yield a concentration $C_3$. However, this concentration $C_3$ is clearly incorrect because the concentration of the component has not changed and is still at a value $C_1$.

This is because concentration, on either a mass or a weight basis, does not change with the temperature of the fluid, even though the fluid's density does. Concentration on a mass basis is simply proportional to the ratio of the concentrate mass divided by the sum of the concentrate mass plus the carrier mass. Mass does not change with temperature and, therefore, neither does concentration on a mass basis. However, density, which defined as mass per volume, does change with temperature since volume typically increases with increasing temperature.

In fact, with the change in density with the change in temperature, a change in the density-concentration relationship has occurred. This changed relationship is indicated by the broken-line curve 16 in FIG. 1 which is drawn through the intersection point between a vertical line drawn up from concentration $C_1$ and the horizontal line drawn from density $\rho_3$. What this second curve 16 illustrates is that, for an accurate concentration determination at the second temperature a different curve (in this case curve 16) should be used.

A seemingly straightforward solution to this problem would be to accurately account for temperature changes. One way of doing this would be to make allowance for the changes in a fluid's density based on its coefficient of thermal expansion. However, a mixture of two components cannot accurately be characterized as having a single, constant coefficient of thermal expansion because the two components will behave differently as temperature changes and will depend on the relative amendment of the two components present which, of course are a priori, unknown. This is primarily because each component of the mixture will exhibit different rates of thermal expansion.

Furthermore, it is not always possible to know or obtain the expansion coefficient for each fluid component. For example, in the case of a sugar solution, one would have to know the expansion coefficient for both water (which is known) and that of sugar in solution (which is not known).

Another way of making allowances for changes in temperature would be to plot a large number of density-concentration curves over a large range of different temperature conditions. Unfortunately, this is not always practical to do for each and every type of solution that one would wish to measure. Furthermore, certain density-concentration measurements are required to be so accurate that temperature differences of only a few degrees Fahrenheit could lead to unacceptable inaccuracies. To produce a curve for each possible temperature range is similarly impractical.

For the above reasons, therefore, the prior art methods of determining density concentration relationships and, more particularly, the concentration of a component of a two-component fluid mixture and its associated flowrate are insufficient for providing for situations where the temperature of the mixture varies.

SUMMARY OF THE INVENTION

Object of the Invention

It is, therefore, an object of this invention to provide a method for determining the concentration and flow rate of a component of a two-component fluid mixture over a range of different temperatures.

Another object of the present invention is to provide a method for measuring the concentration and flow rate of a component of a two-component fluid mixture without having any information about the fluid mixture's thermal expansion coefficient.

Yet another object of this invention is to provide a method of characterizing the density concentration relationship of a two-component fluid mixture over of range of different temperatures.

SUMMARY OF THE INVENTION

Briefly, this invention provides for a method for determining the relationship between the density of a multicomponent fluid mixture comprising a number of known components and the concentration of one of the components of the fluid mixture. The method comprises the steps of:

(i) determining a first and a second density-concentration relationship to define the relationship between the density of the fluid mixture and the concentration of said component at first and second known temperatures $T_1$ and $T_2$, respectively;

(ii) measuring the temperature T of the mixture;

(iii) determining a temperature ratio value according to the relationship $$\frac{T - T_2}{T_1 - T_2};$$

(iv) choosing a component concentration value $C_i$;

(v) determining first and second density values $\rho(C_i, T_1)$ and $\rho(C_i, T_2)$ by inputing said component concentration value $C_i$ into said first and second density-concentration relationships to yield said first and second density values respectively;

(vi) subtracting said second density value from said first density value to produce a density difference value $\Delta\rho_{T_1,T_2}$;

(vii) processing the results from steps (iii), (v) and (vi) according to the equation $$\rho(C_i, T) = \rho(C_i, T_2) + \left[\frac{T - T_2}{T_1 - T_2}\right] \cdot \Delta\rho_{T_1,T_2}$$

to produce a density-concentration value $\rho(C_i, T)$ for said fluid mixture;

(viii) incrementing the initial component concentration to provide a new component concentration value $C_i$; and (ix) repeating steps (v) to (viii) until sufficient density-concentration values have been produced to define said relationship between the density of a multi-component fluid mixture comprising a number of known components and the concentration of one of the components of said fluid mixture.

The method of the invention can further be used to determine the mass flow rate of the component of the multicomponent fluid mixture. This is done by the following additional steps:

(i) measuring the density of the multi-component fluid;

(ii) using the relationship between density and concentration as determined above, to determine the concentration of the component;

(iii) measuring the mass flow rate of the multi-component fluid mixture; and (iv) multiplying said mass flow rate of the fluid mixture by the determined concentration of the component to determine said mass flow rate of the component.

Advantages of this Invention

A primary advantage of the method of this invention is that it provides an accurate manner of determining the relationship between the density of a two-component fluid mixture and the concentration of a component fluid of that mixture.

Another advantage of the method of this invention is that temperature changes are properly accounted for when determining this density concentration relationship.

Yet another advantage of the method of this invention is that knowledge of the thermal expansion coefficients for each component of the two-component fluid mixture is not required in order to accurately derive the density-concentration relationship.

These and other objects and advantages of the present invention will no doubt become apparent to those skilled in the art after having read the following detailed description of the preferred embodiment illustrated in the several figures of the drawing.

BRIEF DESCRIPTION OF AN EMBODIMENT

1. General Overview of the Method

Figure 2:
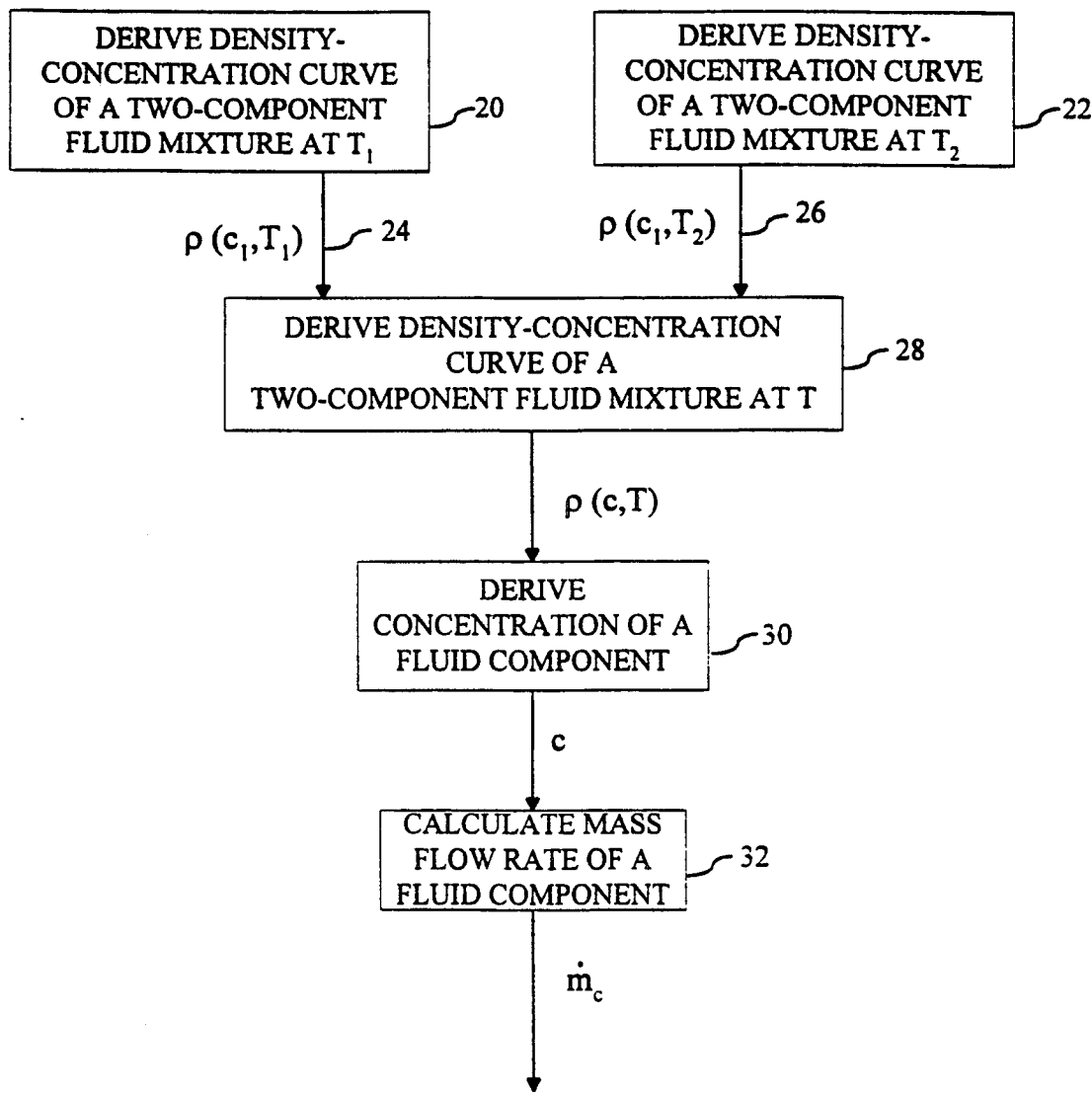
FIG. 2 is a flow chart illustrating the primary steps of the method of this invention.

The primary steps of the method of this invention are illustrated in FIG. 2. It should be understood that this figure gives only an overview of the method of the invention and that a more detailed description thereof is presented in the description of FIGS. 3-5.

Figure 1:
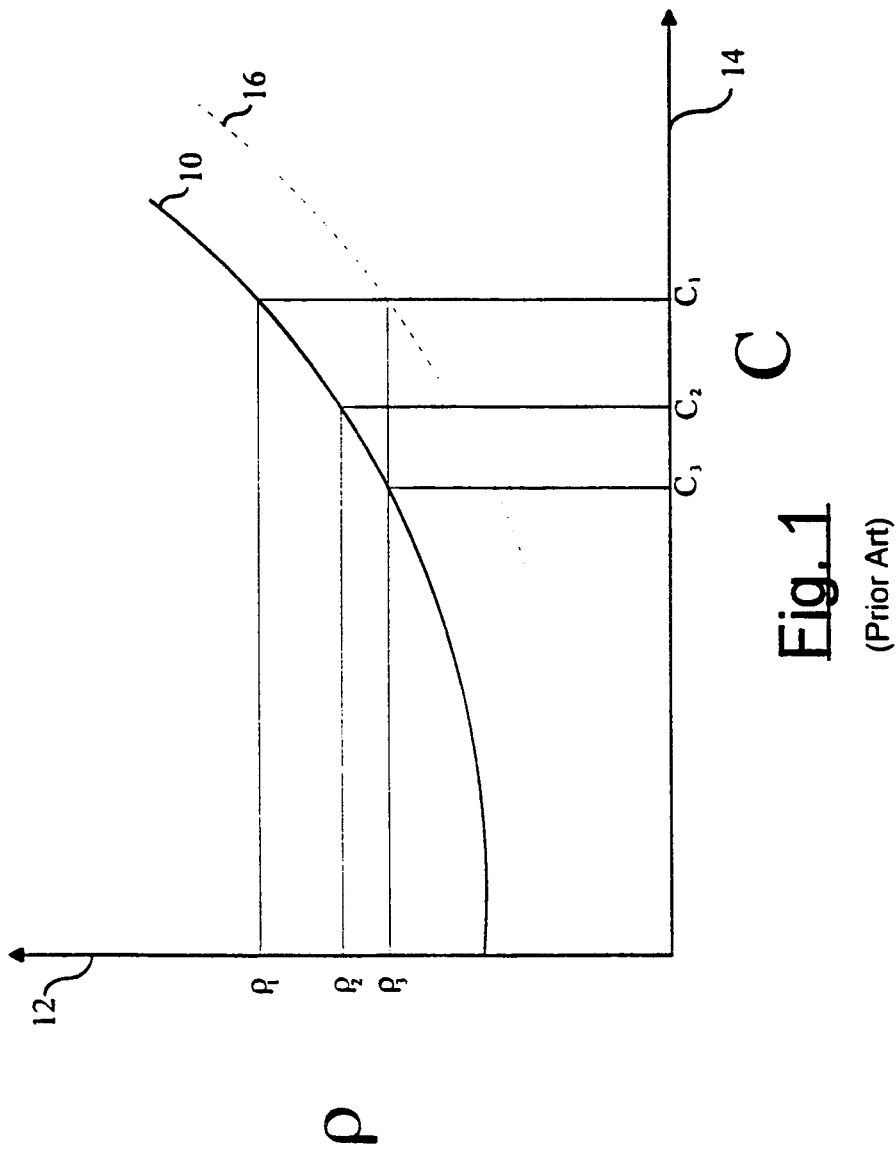
FIG. 1 illustrates a prior art method of determining the density-concentration relationship for a two-component fluid mixture.

The method of this invention, rather than using a single density concentration curve at a single temperature (as shown in FIG. 1), uses two density concentration curves, each determined at a different temperature, to define the density-concentration relationship of the two-component fluid mixture.

The first density concentration curve is produced, at a first temperature $T_1$, according to the method described above with reference to FIG. 1. This step is represented by the block marked 20 in FIG. 2. Similarly, the second curve is derived for the fluid at a second, different temperature $T_2$ during a step represented by the block marked 22. The result of step 20 is a density-concentration relationship, derived at temperature $T_1$ and expressed as $\rho(C, T_1)$, and the result of step 22 is a similar relationship, derived at temperature $T_2$, which can be expressed as $\rho(C, T_2)$.

The next step in the method, represented by the block marked 28, is to derive a density concentration curve of the two-component fluid mixture at a temperature T, which is the actual measured temperature of the two-component mixture under investigation. This step will be described in greater detail below with reference to FIGS. 3 and 4 and yields a new density concentration relationship which can be expressed $\rho(C, T)$.

This new relationship $\rho(C, T)$ is then used, in a further step represented by the block marked 30 to determine the concentration of the fluid component of the two-component fluid mixture at the temperature T. This is done, as is explained above, by measuring the density of the fluid mixture and determining the concentration C using the new relationship $\rho(C, T)$.

Finally, the concentration C is processed in step 32 to calculate the mass flow rate $m_c$ of the fluid component under consideration.

2. Derivation of the $\rho$-C Curve at Temperature T

Figure 3:
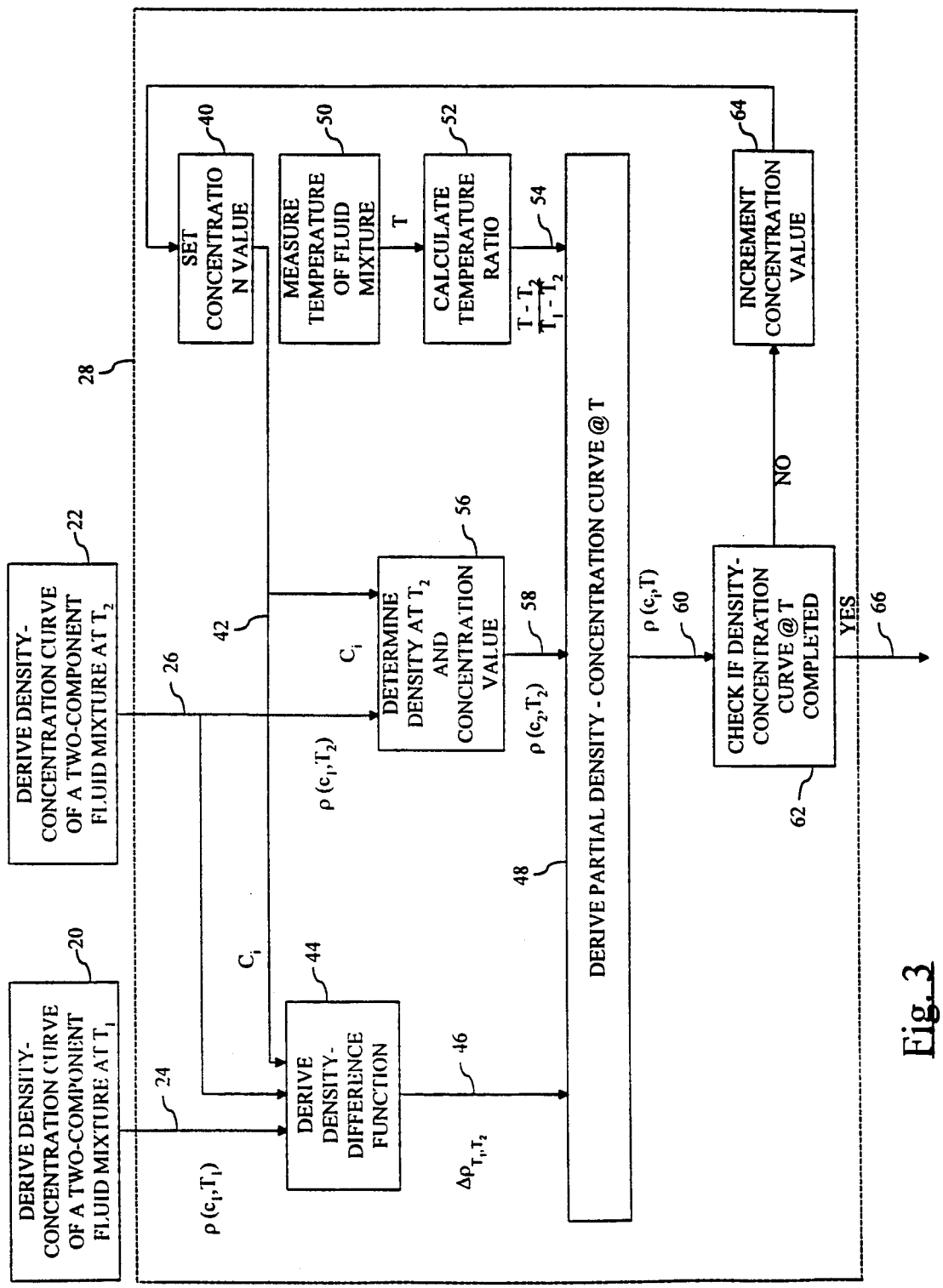
FIG. 3 is a flow chart illustrating, in detail, two of the steps in FIG. 2.

In FIG. 3, which is a flow diagram, the steps 28 and 30 of FIG. 2 are further illustrated.

Starting with an initializing substep 40, an initial concentration value $C_i$ is set. This value $C_i$ is input, along path 42, into substep 44 which derives a density value corresponding to the concentration value $C_i$ for both of the curves produced by steps 20 and 22, respectively. Substep 44 then produces a density difference value by subtracting the two different density values obtained in this way, in accordance with Equation (1):

$$\Delta\rho_{T_1,T_2} = \rho(C_i,T_1) - \rho(C_i,T_2) \tag{1}$$

Figure 4:
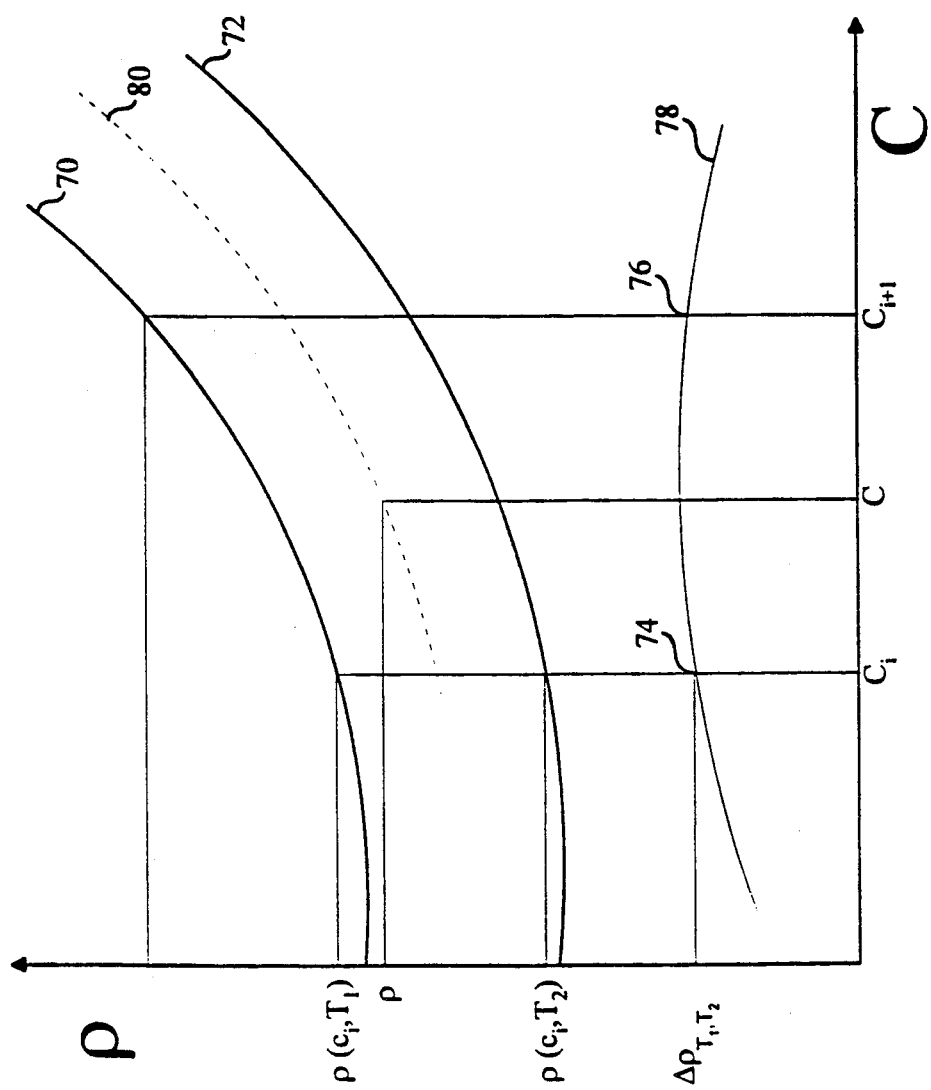
FIG. 4 is a graphical representation further illustrating the steps in FIG. 3.

This substep 44 is graphically illustrated in FIG. 4 in which the density concentration curve $\rho(C, T_1)$, derived by step 20, is illustrated as curve 70 and the density concentration function $\rho(C, T_2)$, derived by step 22 above, is represented by curve 72.

For the initial concentration value $C_i$, the corresponding density values $\rho(C_i, T_1)$ and $\rho(C_i, T_2)$ are read using the curves 70 and 72, respectively. The difference between these two values, i.e., $\Delta\rho_{T_1, T_2}$ corresponds to a point 74 on the vertical line extending from concentration point $C_i$. This point 74 also lies on a density difference curve 78.

Returning now to FIG. 3, it can be seen that the resulting density difference value $\Delta\rho_{T_1, T_2}$ is input along path 46 to substep 48 in which a partial density concentration curve for the mixture at measured temperature T is derived. The substep 48 is further described below.

Also as part of step 28, a substep 50 measures the temperature T of the two-component fluid mixture. The temperature T is then processed in substep 52 which calculates a temperature ratio according to the following Equation (2):

$$\frac{T - T_2}{T_1 - T_2} \tag{2}$$

The resulting temperature ratio is then input along path 54 to be processed in substep 48, along with the density difference value $\Delta\rho_{T_1, T_2}$ derived in this substep 44.

Yet another component of step 28 is substep 56 which utilizes the initially-set concentration $C_i$ and determines, by using the results of step 22, its corresponding density $\rho(C_i, T_2)$ for the fluid mixture at the second temperature $T_2$. The resulting density value $\rho(C_i, T_2)$, is input along path 58 to substep 48.

Substep 48, therefore, uses the density difference value $\Delta\rho_{T_1, T_2}$ produced by substep 44, the density value $\rho(C_i, T_2)$ produced by substep 56 and the temperature ratio produced by substep 52. These values are then used to derive a partial density concentration value $\rho(C_i, T)$ at temperature accordance with Equation (3):

$$\rho(C_i,T) = \rho(C_i,T_2) + \left[\frac{T - T_2}{T_1 - T_2}\right] \cdot \Delta\rho_{T_1,T_2} \tag{3}$$

This value $(C_i, T)$ is then input along path 60 and stored as indicated by substep 62. Substep 62 also checks whether or not enough partial density concentration values have been derived to adequately plot density concentration curve at temperature T. If this substep 62 finds that insufficient data points exist, substep 64 increments the concentration value $C_i$ to $C_{i+1}$, and the above process is repeated.

This step is graphically illustrated in FIG. 4 in which, during the iteration represented by substep 64, the concentration is incremented to a value $C_{i+1}$. This concentration $C_{i+1}$, following the method above, yields a further $\Delta\rho_{T_1, T_2}$ point 76 on the vertical line extending from point $C_{i+1}$.

The curve 78 drawn through points 74 and 76 and other derived points (not illustrated) is the graphical representation of the relationship defined by Equation (1) above.

Once sufficient values for $\rho(C_i, T)$ have been produced in terms of Equation (3), the resultant function $\rho(C, T)$ is input along path 66 to step 30. This function $\rho(C, T)$ is graphically represented by curve 80 in FIG.

4 which, in fact, represents the density concentration value for the mixture under study at measured temperature T.

As illustrated in this FIG, measured temperature T is less than temperature $T_2$, but is greater than $T_1$, but it will be apparent that the method of this invention could be applied to the mixture at any temperature T, whether it was greater than or less than both temperatures $T_1$ or $T_2$.

3. Derived Concentration of the Fluid Component

Figure 5:
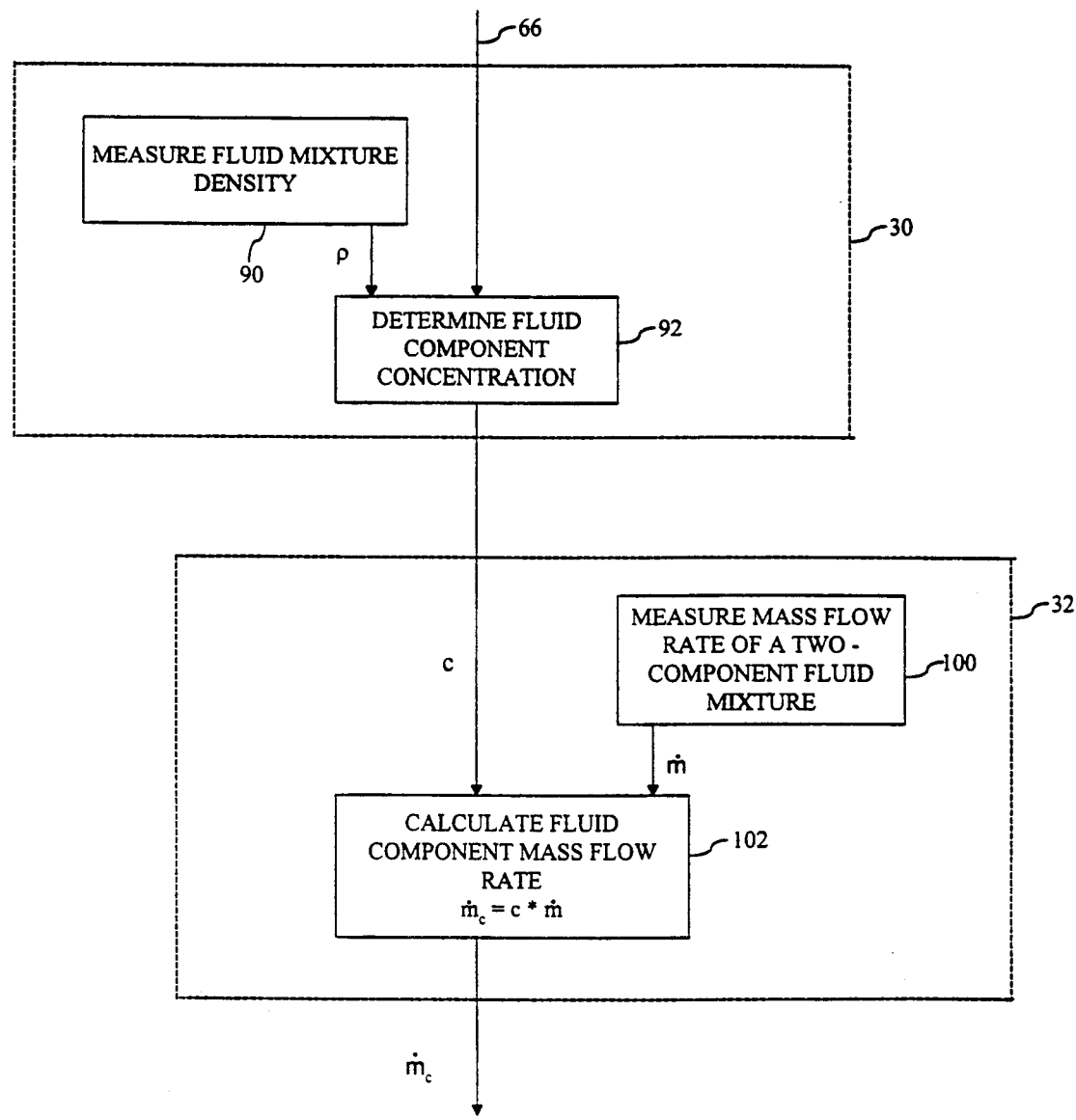
FIG. 5 is a flow chart illustrating, in detail, the final two steps of FIG. 2.

The step of deriving the concentration C of the fluid component of the two-component mixture is illustrated in greater detail in the top half of FIG. 5.

Initially, the density of the fluid mixture must be measured in connection with substep 90. This density value $\rho$ is then input into substep 92 which uses the density concentration curve 80 illustrated in FIG. 4 to read off the fluid concentration value C.

4. Calculation of the Mass Flow Rate

Thereafter, the concentration value C is input into step 32, shown in the lower half of FIG. 5, to determine the mass flow rate of the fluid component under consideration.

Step 32 is, in itself, a two-step procedure wherein, in the first substep 100, the mass flow rate m of the entire two-component fluid mixture is measured. This can be done using any convenient method, but a Coriolis flow meter, employing at least one vibrating tube, is a preferred device for measuring flow rates and, for that matter, the fluid density in substep 90 described above. A suitable Coriolis mass flow of this type is described in U.S. patent application Ser. No. 07/833,767, the disclosure of which is incorporated herein by reference.

Once the mass flow rate m has been determined, this is input into the final substep 102 where the mass flow rate of the fluid component $m_c$ can be calculated according to the following Equation (4):

$$m_c = C \times m \quad (4)$$

5. Application of the Method of the Invention

The method of this invention provides an accurate method of determining the concentration and the mass flow rate of a fluid component in a two-part fluid mixture.

It will be appreciated by anyone skilled in the art that this method has many applications and can be used in any of a large number of industrial applications which require knowledge of the concentration and/or mass flow rate of a component in a two-part fluid mixture.

Although a preferred embodiment of the present invention has been disclosed above, it will be appreciated that numerous alterations and modifications thereof will no doubt become apparent to those skilled in the art after having read the above disclosures. It is therefore intended that the following claims be interpreted as covering all such alterations and modifications as fall within the true spirit and scope of the invention.

What is claimed is:

1. A method for defining the relationship between the density of a multi-component fluid mixture and the concentration of one of the components of said fluid mixture, the method comprising the steps of:
   (i) determining a first density-concentration relationship defining the relationship between the density of said fluid mixture and the concentration of said component at a first known temperature $T_1$;
   (ii) determining a second density-concentration relationship defining the relationship between the density of said fluid mixture and the concentration of said component at a second known temperature $T_2$;
   (iii) measuring the temperature T of said mixture;
   (iv) determining a temperature ratio value according to the equation $$\frac{T - T_2}{T_1 - T_2};$$

(v) choosing a component concentration value $C_i$;
   (vi) inputing said component concentration value $C_i$ into said first density-concentration relationship to determine a first density value $\rho(C_i, T_1)$;
   (vii) inputing said component concentration value $C_i$ into said second density-concentration relationship to determine a second density value $\rho(C_i, T_2)$;
   (viii) subtracting said second density value from said first density value to produce a density difference value $\Delta\rho_{T1,T2}$;
   (ix) processing the results from steps (iv), (vii) and (viii) according to the equation $$\rho(C_i, T) = \rho(C_i, T_2) + \left[\frac{T - T_2}{T_1 - T_2}\right] \cdot \Delta\rho_{T1,T2}$$

to produce a density-concentration value $\rho(C_i, T)$ for said fluid mixture;
   (x) incrementing the component concentration to provide a new component concentration value $C_i$;
   (xi) repeating steps (v) to (x) until sufficient density-concentration values have been produced to define said relationship between the density of said mixture and said concentration of one of the components of said fluid mixture.

2. A method of determining the mass flow rate of a component of a multi-component fluid mixture comprising the steps as set out in claim 1 and further comprising the steps of:
   (i) measuring the density of said multi-component fluid;
   (ii) using said defined relationship between the density of said mixture and the concentration of one component of said mixture to determine the concentration of said component;
   (iii) measuring the mass flow rate of said mixture; and
   (iv) multiplying said measured mass flow rate by said determined concentration of said component to determine said mass flow rate of said component.

3. The method of claim 2 wherein said mass flow rate of the fluid mixture is measured using a Coriolis mass-flow meter.

4. The method of claim 3 wherein said mass flow rate of the fluid mixture is measured using a Coriolis mass-flow meter which includes at least one vibrating tube.

5. The method of claim 1 wherein said first and second density-concentration relationships are each determined according to a method comprising the steps of:
   (i) creating a sample of said multi-component fluid mixture in which the concentration of said component is known and heating said mixture to said known temperature;
   (ii) measuring the density of said fluid mixture;

(iii) defining a density-concentration value representing said known concentration and said measured density;

(iv) creating a different sample of said fluid mixture with a different concentration of said component and heating said fluid mixture to said known temperature; and (v) repeating steps (ii) to (iv) until sufficient density-concentration values have been defined to determine said density-concentration relationship.

6. The method of claim 5 wherein said density is determined using any one of the devices in a group consisting of a pycnometer, a vibrating tube densitometer, gamma ray density gauges, and hygrometers.

* * * * *